United States Patent [19]

Gibson et al.

[11] Patent Number: 4,996,346

[45] Date of Patent: Feb. 26, 1991

[54] FORMATION OF ACYCLIC BIS (REISSERT COMPOUNDS)

[75] Inventors: Harry W. Gibson; Yajnanarayana H. R. Jois, both of Blacksburg, Va.

[73] Assignee: Virginia Tech Intellectual Properties, Inc., Blacksburg, Va.

[21] Appl. No.: 418,365

[22] Filed: Oct. 6, 1989

[51] Int. Cl.$^5$ .......................................... C07C 255/29
[52] U.S. Cl. .................... 558/392; 558/388; 558/390
[58] Field of Search .......................................... 558/392

[56] References Cited

U.S. PATENT DOCUMENTS 4,242,273 12/1980 Shepard ................................ 564/91

OTHER PUBLICATIONS (I) Radhakrishnan et al., "Synthesis and Reactions of an Open-Chair etc.", J. Heterocyclic Chem., 23, pp. 991-997, 1986.

McEwen et al., "Synthetic Uses of Open-Chain Analogues, et al.", J. Org. Chem. 45, pp. 1301-1308 (1980).

Huh et al., "Crossed-Beam Study of HX Elimination Rxns", CA 109, 92061r, 1988.

(II) Radhakrishnan et al., "Synthesis of a Bis-Alpha amino Acid", CA 101, 192413k, 1984.

Primary Examiner—Glennon H. Hollrah
Attorney, Agent, or Firm—Richard P. Fennelly; Louis A. Morris

[57] ABSTRACT

Bis Reissert compounds can be formed by reaction of a cyanohydrin, formed by reaction of an aldehyde and a diamine, with benzoyl chloride in the presence of an amine acid acceptor.

5 Claims, No Drawings

FORMATION OF ACYCLIC BIS (REISSERT COMPOUNDS)

BACKGROUND OF THE INVENTION

Recently, it has been proposed that Reissert compounds be synthesized to develop novel heterocyclic polymers for high performance applications (see H. W. Gibson et al., Amer. Chem. Soc., Polymer Preprints, 29(1), 154, 1988). Bis (Reissert compounds) have been synthesized in excellent yields by the use of a trimethylsilyl cyanide reagent and can be used to develop such polymers (see A. Pandya et al., Amer. Chem. Soc., Polymer Preprints, 30(1), 206, 1989). Several novel 4,4'-coupled bis-isoquinolines have also been synthesized (see H. W. Gibson et al., Amer. Chem. Soc., Polymer Preprints, 30(1), 208, 1989).

W. E. McEwen et al., in J. Org. Chem. 1980, 45, 1301-1308 discuss the synthetic uses of open-chain analogues of Reissert compounds by first preparing an aminonitrile by condensation of a primary amine with a cyanohydrin followed by reaction of the aminonitrile with an acid chloride to form the Reissert compound.

Chemical Abstracts, Vol. 87, 202161k reports on work by N. Voznesenskaya et al. in 1977 relating to the preparation of poly(phenyleneimidazolones) by polymerization of bis(alpha-aminonitriles) with aromatic dicarboxylic acid chlorides and subsequent cyclization of the prepared poly(alpha-cyanamides) by isomerization.

DESCRIPTION OF THE INVENTION

The starting cyanohydrin reagent of the formula

RCH(CN)NH(R')NHCH(CN)R where R is alkyl (e.g., ethyl) and R' is alkylene (e.g., —(CH$_2$)$_6$—) can be initially formed by reaction of an aldehyde (RCHO) and diamine (H$_2$N—R'—NH$_2$) in the presence of a cyanide source (e.g., NaCN) and bisulfite (e.g., sodium bisulfite). The molar ratio of aldehyde to diamine may vary from about 1:2 to about 1:3. The molar ratio of cyanide and bisulfite to aldehyde may vary from about 1:1 to about 1.6:1 in both cases. The reaction may be conducted in aqueous solution at temperatures of from about 0° C. See Organic Synthesis, Col. Vol. 4, p. 437.

Reaction of the cyanohydrin described above with benzoyl chloride in the presence of an appropriate amine acid acceptor (e.g., pyridine) yields the desired bis Reissert compound of the formula

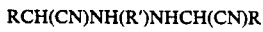

RCH(CN)N(R')NCH(CN)R
     |     |
    PhCO  OCPh where R and R' are as defined above and Ph is phenyl.
The following Examples illustrate the invention.

EXAMPLE 1

This illustrates formation of the cyanohydrin reagent depicted above where R is ethyl and R' is (CH$_2$)$_6$.

A mixture of water (300 ml) and sodium bisulfite (1.2 moles, 125 gm) in a one liter beaker equipped with a mechanical stirrer was stirred until solution was complete. Propionaldehyde (1.2 moles, 87 ml) was added, and the mixture was stirred for one hour. Then, 1,6-hexanediamine (0.6 mole, 7 1.2 gm) in water (150 ml) was added. This was followed by the addition of sodium cyanide (1.2 moles, 59 gm) over a thirty minute period. The reaction mixture was stirred overnight, was extracted with ether (3×300 ml) and dichloromethane (1×300 ml). The organic layers were combined, were washed with water (2×200 ml), were dried over magnesium sulfate and were concentrated to yield 85.5 gm (56%) of crude product which was purified by double distillation (b.p. =110° C./1.5 mm Hg).

IR (neat): 3700-3100 (NH), 3000-2800 (C—H), 2223 (weak, CN), 1665, 1634, and 1461 cm$^{-1}$.

$^1$H NMR (CDCl$_3$): delta 3.47 (t, 2H, CHCN), 2.93-2.82 (m, 2H, NH), 2.72-2.54 (m, 4H, NCH$_2$), 1.88-1.70 (m, 4H, CH$_2$CH$_2$), 1.60-1.30 (m, 8H, 4 CH$_2$), and 1.09 (t, 6H, CH$_3$).

EXAMPLE 2

This Example illustrates reaction of the previously defined cyanohydrin reagent where R is ethyl and R' is (CH$_2$)$_6$.

To a well stirring solution of 0.01 mole (2.5 gm) of a compound I:

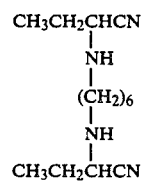

in pyridine (12 ml), was added benzoyl chloride 0.02 mole (2.32 ml) at 0°-5° C. The reaction mixture was stirred at room temperature for thirty-six hours under dry conditions. The reaction mixture was then quenched by pouring into water (300 ml) and was extracted with dichloromethane (3×75 ml). The organic layer was washed with 8% aqueous HCl (3×50 ml), aqueous saturated sodium bicarbonate (3×50 ml), water (3×50 ml), and was dried over magnesium sulfate, and concentrated to yield 5.46 gm (essentially 100% of the following bis Reissert compound:

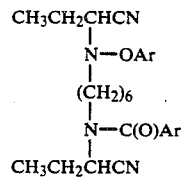

where Ar represents phenyl. When purified by crystallization from ethanol it had a melting point of 110°-111° C.

IR (KBr): 3065-2860 (C—H), 2243 (weak CN), 1633 (N—CO), 1601, 1579 (aromatic), 1494, 1466, 1435, 1413, 1382, 1370, 1352, 1324, 1316, and 1283 cm$^{-1}$.

$^1$H NMR (DMSO-d$_6$): delta 7.55-7.35 (m, 1OH, COC$_6$H$_5$), 4.84 (s, 2H, CHCN), 3.3-3.1 (m, 4H, NCH$_2$), 2.1-1.85 (m, 4H, CH$_2$CH$_3$), 1.1-0.8 (m, 14H, CH$_3$ and 4 CH$_2$).

We claim;

1. A process for the formation of a bis Reissert compound of the formula

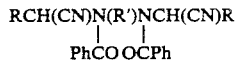

where R is alkyl, R' is alkylene, and Ph is phenyl which comprises reaction of

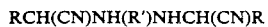

with benzoyl chloride in the presence of pyridine as amine acid acceptor.

2. A process as claimed in claim 1 where R is ethyl.
3. A process as claimed in claim 1 wherein R' is $(CH_2)_6$.
4. A bis Reissert compound of the formula

where R is alkyl, R' is $C_6$ alkylene and Ph is phenyl.
5. A compound as claimed in claim 4 where R is ethyl.

* * * * *